United States Patent
Miller

(10) Patent No.: US 7,211,065 B2
(45) Date of Patent: May 1, 2007

(54) ENVELOPING NEEDLE STICK PROTECTION DEVICE

(76) Inventor: Stuart H. Miller, 16 E. Eighth St., Clifton, NJ (US) 07011-1102

( * ) Notice: Subject to any disclaimer, the term of this patent is extended or adjusted under 35 U.S.C. 154(b) by 88 days.

(21) Appl. No.: 10/934,413

(22) Filed: Sep. 7, 2004

(65) Prior Publication Data

US 2005/0187522 A1    Aug. 25, 2005

Related U.S. Application Data

(60) Provisional application No. 60/545,527, filed on Feb. 19, 2004.

(51) Int. Cl.
*A61M 5/00* (2006.01)

(52) U.S. Cl. .................. 604/110; 604/192; 604/198
(58) Field of Classification Search ............ 604/110, 604/111, 187, 192, 195–198, 181
See application file for complete search history.

(56) References Cited

U.S. PATENT DOCUMENTS

| | | | |
|---|---|---|---|
| 4,813,940 A * | 3/1989 | Parry | 604/198 |
| 5,106,379 A | 4/1992 | Leap | |
| 5,472,430 A | 12/1995 | Vaillancourt et al. | |
| 5,591,138 A | 1/1997 | Vaillancourt | |
| 5,795,336 A | 8/1998 | Romano et al. | |
| 5,984,899 A * | 11/1999 | D'Alessio et al. | 604/198 |
| 6,183,445 B1 * | 2/2001 | Lund et al. | 604/198 |
| 6,322,540 B1 | 11/2001 | Grabais et al. | |
| 6,325,781 B1 * | 12/2001 | Takagi et al. | 604/198 |
| 6,344,032 B1 * | 2/2002 | Perez et al. | 604/198 |
| 6,969,376 B2 * | 11/2005 | Takagi et al. | 604/263 |
| 2003/0144630 A1 | 7/2003 | Chang et al. | |

* cited by examiner

*Primary Examiner*—Kevin C. Sirmons
*Assistant Examiner*—Laura C. Schell
(74) *Attorney, Agent, or Firm*—Welsh & Flaxman LLC

(57) ABSTRACT

A needle stick protection device includes a housing shaped and dimensioned for positioning about a needle. The housing includes a first housing member telescopically coupled to a second housing member. The first housing member includes an open first end and an open second end. The second housing member includes an open first end and a substantially closed second end, the second end including an aperture shaped and dimensioned to permit the passage of a needle therethrough. The device also includes a mechanism for locking the first housing member relative to the second housing member wherein the second housing member moves relative to the first housing member to facilitate retraction and extension of the needle through the aperture at the second end of the second housing member. The second housing member is biased relative to the first housing member in a manner forcing the first end of the second housing member away from the first end of the first housing member to maintain the second housing member in a cover position in which the needle is fully contained within the housing.

8 Claims, 3 Drawing Sheets

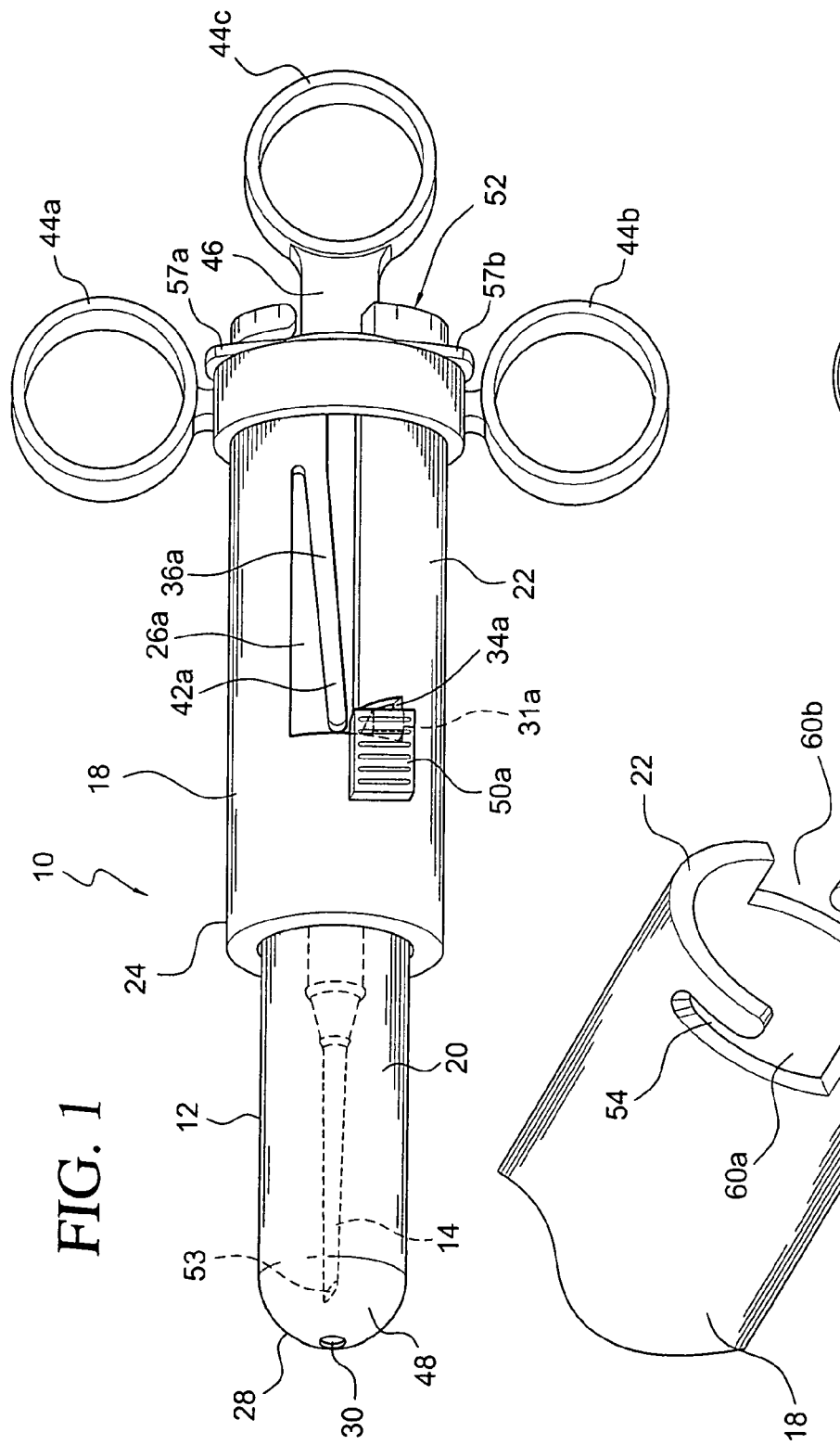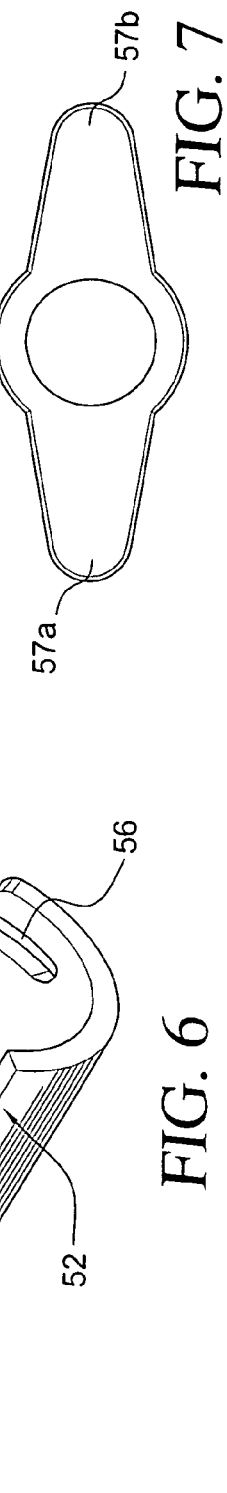

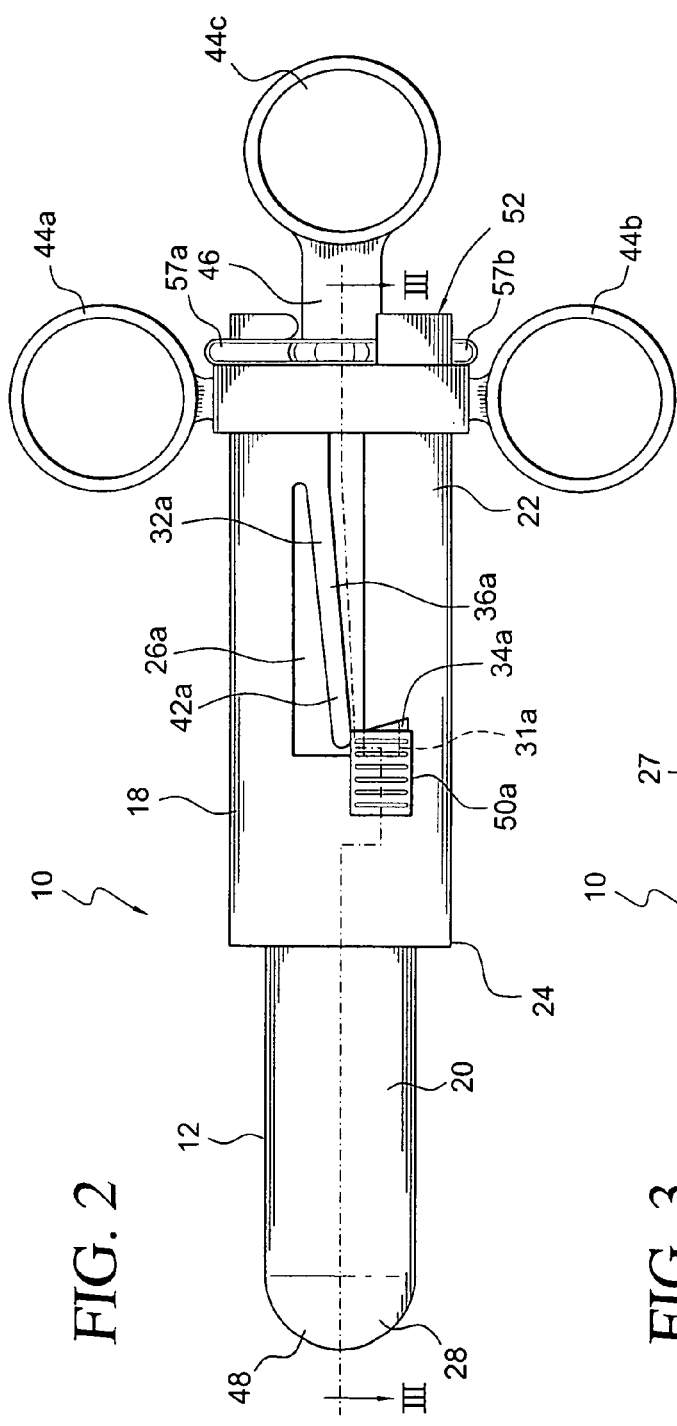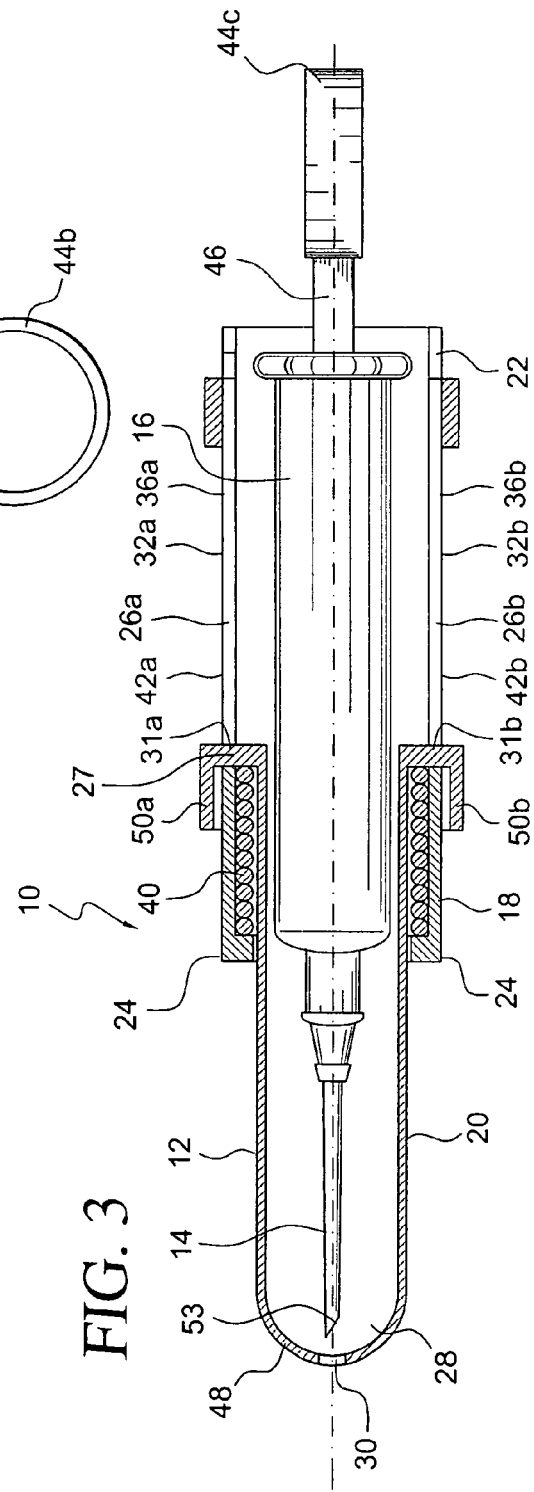

ENVELOPING NEEDLE STICK PROTECTION DEVICE

CROSS REFERENCE TO RELATED APPLICATIONS

This application claims priority of U.S. Provisional Application Ser. No. 60/545,527, entitled "NEEDLE STICK DEVICE", filed Feb. 19, 2004.

BACKGROUND OF THE INVENTION

1. Field of the Invention

The invention relates to a device for preventing needle sticks. More particularly, the invention relates to a device for preventing needle sticks wherein the needle is selectively locked and released relative to a shielding device.

2. Description of the Prior Art

As those within the medical field have developed an understanding that a variety of diseases may be transferred via unclean and previously used needles, many devices have been developed for protecting medical practitioners and other individuals from previously used needles. Many currently available needle stick protection devices operate by either withdrawing the used needle into a hard protective shell or extending a hard protective shell over the used needle. These devices are generally utilized once and are then discarded in an approved collection device.

While most procedures permit the disposal of needles after a single usage, some medical procedures require that needles be used more than once during a procedure on a patient. However, these used needles may be passed between physicians and other medical practitioners several times during the procedure. As such, a possibility exists that physicians and other medical practitioners may be stuck with these used needles during the procedure.

A need, therefore, exists for a needle stick protection device in which the needle is selectively shielded and unshielded as the medical procedure dictates. The present invention provides such a needle stick protection device.

SUMMARY OF THE INVENTION

It is, therefore, an object of the present invention to provide a needle stick protection device including a housing shaped and dimensioned for positioning about a needle. The housing includes a first housing member telescopically coupled to a second housing member. The first housing member includes an open first end and an open second end. The second housing member includes an open first end and a substantially closed second end, the second end including an aperture shaped and dimensioned to permit the passage of a needle therethrough. The device also includes a mechanism for locking the first housing member relative to the second housing member wherein the second housing member moves relative to the first housing member to facilitate retraction and extension of the needle through the aperture at the second end of the second housing member. The second housing member is biased relative to the first housing member in a manner forcing the first end of the second housing member away from the first end of the first housing member to maintain the second housing member in a cover position in which the needle is fully contained within the housing.

It is also an object of the present invention to provide a needle stick protection device wherein the housing is transparent.

It is another object of the present invention to provide a needle stick protection device wherein the mechanism for locking includes a slot extending longitudinally along the length of the first housing member.

It is a further object of the present invention to provide a needle stick protection device wherein the mechanism for locking further includes an extending detent coupled to the second housing member and extending through the slot for guiding the second housing member relative to the first housing member as the first and second housing members telescopically move relative to each other.

It is also another object of the present invention to provide a needle stick protection device wherein the mechanism for locking further includes a locking member associated with the slot of the first housing member for selectively engaging the detent to control positioning of the second housing member relative to the first housing member.

It is yet another object of the present invention to provide a needle stick protection device wherein the locking member includes a lateral recess formed within the slot for seating of the detent when the second housing member is in its forward most position.

It is also an object of the present invention to provide a needle stick protection device wherein the locking member also includes a spring biased lock arm biasing the detent within the lateral recess when the second housing member is in its forward most position.

It is also another object of the present invention to provide a needle stick protection device wherein the second housing member includes a slide actuating portion for moving the second housing member relative to the first housing member.

It is also a further object of the present invention to provide a needle stick protection device wherein the first housing member includes means for selective attachment to a syringe.

It is still a further object of the present invention to provide a needle stick protection device wherein the means for selective attachment includes a pair of opposed slots at the first and of the first housing member, the opposed slots being shaped and dimensioned for receipt of the syringe.

It is another object of the present invention to provide a needle stick protection device including a spring positioned between the first housing member and the second housing member.

It is also an object of the present invention to provide a needle stick protection device wherein the spring urges the first housing member and the second housing member to a fully telescoped positioned in which the needle is exposed.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 1 is a side perspective view of the present needle stick protection device.

FIG. 2 is a side view of the needle stick protection device with the needle covered.

FIG. 3 is a cross sectional view of the needle stick protection device shown in FIG. 2.

FIG. 6 is a detailed perspective view of the first housing member showing the closure portion.

FIG. 7 is a detailed top view showing the opposed ears of the syringe.

DESCRIPTION OF THE PREFERRED EMBODIMENT

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

Figure 4:
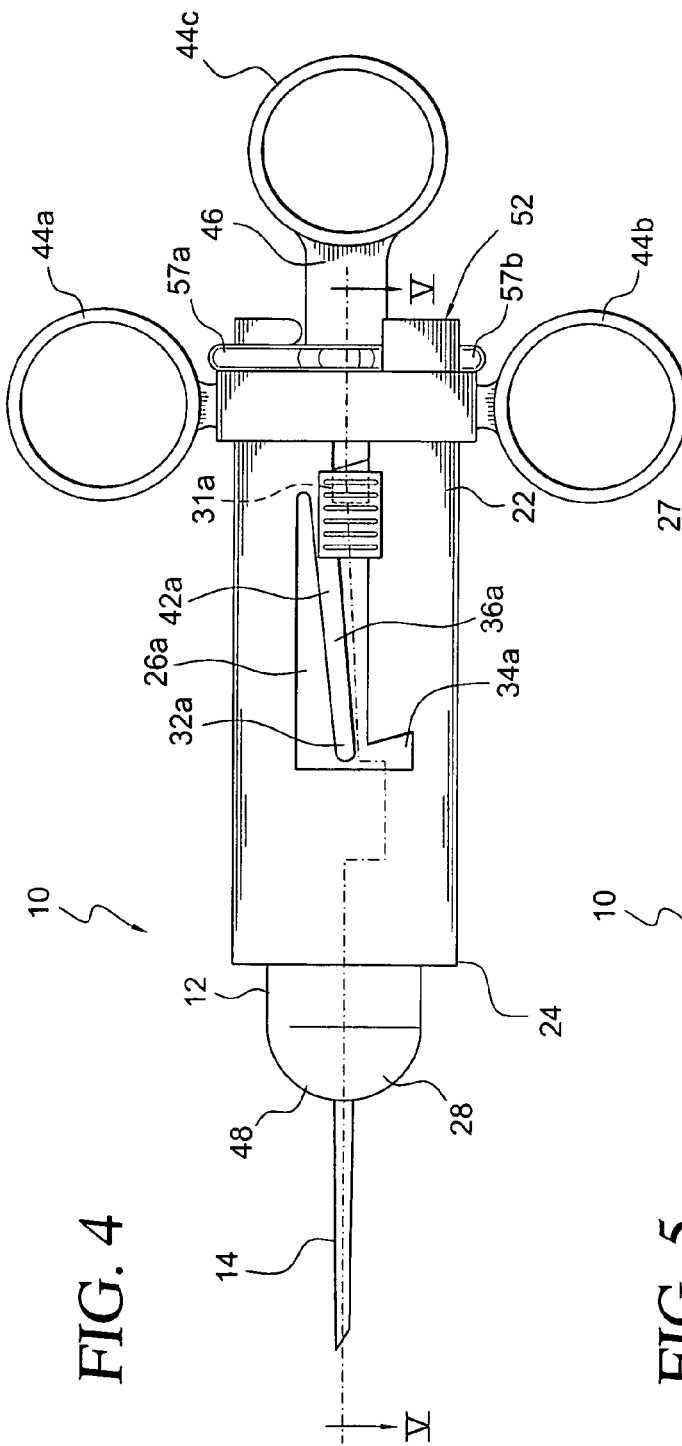
FIG. 4 is a side view of the needle stick protection with the needle exposed.
Figure 5:
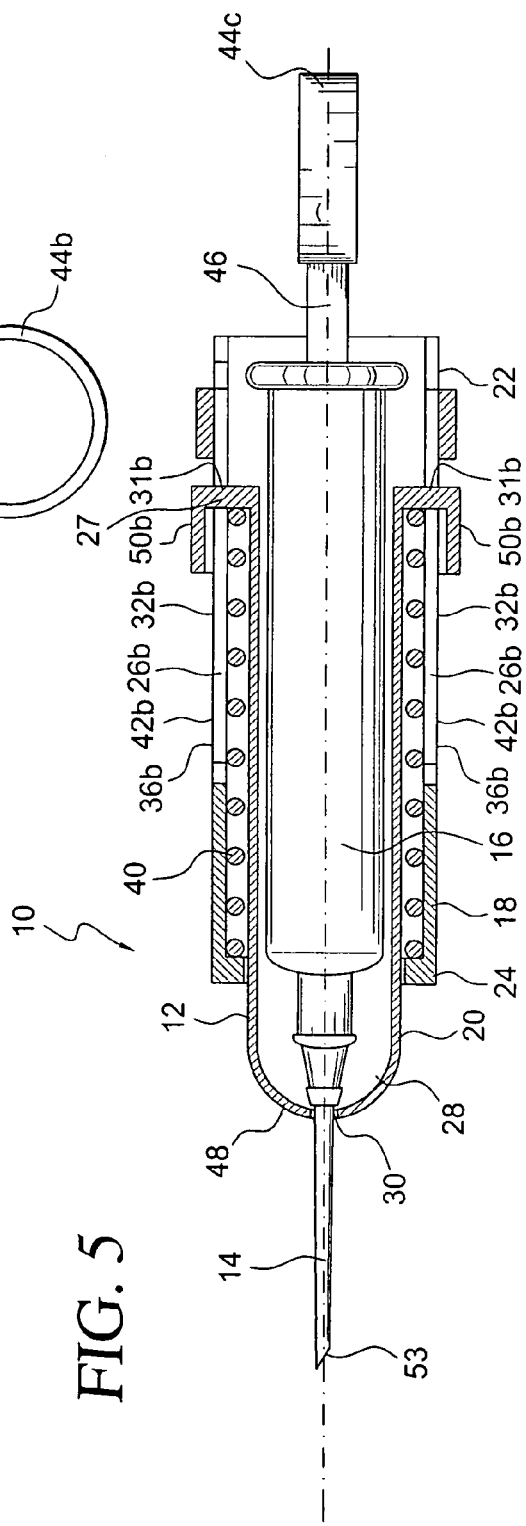
FIG. 5 is a cross sectional view of the needle stick protection device shown in FIG. 4.

With reference to FIGS. 1 to 7, a needle stick protection device 10 is disclosed. The needle stick protection device 10 includes a housing 12 shaped and dimensioned for positioning about a needle 14 and an associated syringe 16. The housing 12 includes a first housing member 18 telescopically coupled to a second housing member 20. The first housing member 18 includes an open first end 22 and an open second end 24. The first housing member 18 further includes slots 26a, 26b extending longitudinally along the length of the first housing member 18 along opposite sides of the first housing member 18.

The second housing member 20 includes an open first end 27 and a substantially closed second end 28. The second end 28 includes an aperture 30 shaped and dimensioned to permit the passage of the needle 14 therethrough. The second housing member 20 further includes detents 31a, 31b extending through the slots 26a, 26b for guiding the second housing member 20 relative to the first housing member 18 as the first and second housing members 18, 20 telescopically move relative to each other.

The needle stick protection device 10 also includes a locking member 32a, 32b associated with each of the slots 26a, 26b of the first housing member 18 for selectively engaging the detents 31a, 31b to control positioning of the second housing member 20 relative to the first housing member 18. Each locking member 32a, 32b includes a lateral recess 34a (only one shown although they are identical) formed within the slot 26a, 26b for seating of the detent 31a, 31b when the second housing member 20 is in its forward most position and a spring biased lock arm 36a, 36b biasing the detent 31a, 31b within the lateral recesses 34a when the second housing member 20 is in its forward most position (see FIGS. 1, 2 and 3). In addition to functioning in the locking of the present device 10, the interaction between the detents 31a, 31b and the slots 26a, 26b keeps the first and second housing members 18,20 aligned and limits the relative travel between the first and second housing members 18,20.

In use, the second housing member 20 moves relative to the first housing member 18 to facilitate retraction and extension of the needle 14 through the aperture 30 of the second end 28 of the second housing member 20. With this in mind, the second housing member 20 is biased relative to the first housing member 18 in a manner forcing the first end 27 of the second housing member 20 away from the first end 22 of the first housing member 18 to maintain the second housing member 20 in a covered position in which the needle 14 is fully contained within the housing 12.

The manually operated second housing member 20 is axially driven by a coil spring 40 relative to the first housing member 18 such that the second housing member 20 covers and uncovers the entire needle 14. The second housing member 20 is automatically locked in position relative to the first housing member 18 by the spring biased lock arms 36a, 36b in the form of one or more cantilevered beams 42a, 42b to provide positive needle stick protection when the second housing member 20 is in its fully extended position. The present needle stick protection device 10 is designed to work with a conventional three-finger syringe arrangement 44a–c commonly utilized within the industry and thereby provides the ability to push and pull on the syringe plunger 46. By using transparent plastic in the construction of the present needle stick protection device 10, the device 10 enables the physician to readily see the contents of the syringe 16.

With regard to the housing 12 and in particular the second housing member 20, it is essentially a cylindrical tube which is open at the first end 27 and has a integral, hemispherical closure 48 at the second end 28. The hemispherical closure 48 has a centrally located aperture 30 through which the needle 14 can freely pass as the second housing member 20 is moved axially to cover and uncover the needle 14. The open first end 27 of the second housing member 18 is fitted with slide actuating portions 50a, 50b for example, pins, cylindrical thumb pads, etc., which are used to manually extend the second housing member 20 so that it covers the entire needle 14. In accordance with a preferred embodiment, the slide actuating portions 50a, 50b are thumb pads which extends from the respective detents 31a, 31b passing through the slots 26a, 26b.

The second housing member 20 is locked in place by the spring biased lock arms 36a, 36b to provide needle protection. As the second housing member 20 slides axially to cover the needle tip 53, each of the spring biased lock arms 36a, 36b are deflected by the respective thumb pads 50a, 50b and the detents 31a, 31b used to slide the second housing member 20. When the second housing member 20 is fully extended, so that the needle 14 is completely covered, the spring biased lock arms 36a, 36b force the thumb pads 50a, 50b and detents 31a, 31b into the recess 34a circumferentially located along the side of the slot 26a, 26b. When in this position, the second housing member 20 cannot be retracted until the thumb pad 50a, 50b and detent 31a, 31b are again aligned with the slot 26a, 26b. When the alignment is achieved, the compressed coil spring 40 positioned between the first and second housing members 18, 20 automatically returns the second housing member 20 to the axial location at which the needle 14 is uncovered. Thus, the second housing member 20 can be used to cover and uncover the needle 14, as required by the physician, so that needle sticks are prevented when the present needle stick protection device 10 is passed back and forth between physician and medical technicians.

A closure portion 52 is selectively coupled to the finger holes 49 of the syringe 16 and is also permanently affixed to the first end 22 of the first housing member 18. The first housing member 18 is also adapted to constrain the coil spring 40 used in retracting the first housing member 18 and uncovering the needle 14.

The spring biased lock arms 36a, 36b are an integral part of the first housing member 18. They are designed to produce circumferential forces on the thumb pads 50a, 50b, as the thumb pads 50a, 50b are manually moved along the slots 26a, 26b. When the thumb pads 50a, 50b reach the circumferentially located recesses 34a, the spring biased lock arms 36a, 36b force the thumb pads 50a, 50b and detents 31a, 31b into the recess 34a, so that the second housing member 20 cannot be moved relative to the first housing member 18, thereby providing needle stick protection. When the thumb pads 50a, 50b are manually moved out of the recesses 34a, through the application of finger pressure in appropriate directions to overcome the bias of the spring biased lock arms 36a, 36b, the compressed coil spring 40 returns the second housing member 20 to the position where the needle 14 is uncovered.

In accordance with preferred embodiments of the present invention, two design configurations are contemplated for use in conjunction with the helical compression spring 40. Specifically, and in accordance with preferred embodiments of the present invention, the following criteria are contemplated for use in conjunction with the first and second springs:

|  | Spring 1 | Spring 2 |
| --- | --- | --- |
| Wire Gage | 18 Ga | 17 Ga |
| Wire Diameter | 0.047" | 0.054" |
| Mean Coil Diameter | 0.827" | 0.802" |
| Coil Pitch | 0.151" | 0.14" |
| Number of Active Cells | 15 | 16 |
| Unloaded Spring Length | 2 1/2" | 2 1/2" |
| Spring Rate | 0.82#/in. | 1.45#/in. |
| Loaded Deflection | 1 1/2" | 1 1/2" |
| Spring OD When Compressed to Solid | 0.877" | 0.860" |
| Solid height for springs with ground ends | 0.783" | 0.964" |
| Solid height for springs with unground ends | 0.830" | 1.018" |

As mentioned above, the device 10 further includes a closure portion 52 affixed to the first end 22 of the first housing member 18. The closure portion 52 is cylindrical and is shaped and dimensioned to be permanently affixed at the first end 22 of the first housing member 18. One end of the closure portion 52 contains two slots 54, 56 at 180° to accept two ears 57a, 57b formed along the actuating plunger 46 of the syringe 16. The geometry of the slots 54, 56 is such that the ears 57a, 57b of the syringe plunger 46 are held in place by an interference fit. The syringe 16 is placed into the recesses 60a, 60b in the closure portion 52 and rotated circumferentially to lock the ears 57a, 57b of the syringe plunger 46 to the closure portion 52 thereby locking the syringe 16 in the needle stick protection device 10. The syringe 16 may be locked in place using finger pressure. The two lateral finger holes 44a, 44b are permanently affixed to the closure portion 52 and are located at 90° from the slots 54, 56 in the first housing member 18 and 180° from each other.

In use, the present needle stick protection device 10 can be completely assembled and will function with or without the syringe 16 in place. The entire syringe 16 with the needle 14 attached is placed in the needle stick protection device 10 and is locked in the closure portion 52. The physician can then expose the needle 14 as described above, insert the needle 14 into the patient as many times as necessary, shielding and unshielding the needle 14 each time it is transferred back and forth between the physician and the medical technician. As mentioned above, since the needle stick protection device is made of transparent plastics, the physician can readily determine when the needle is in a blood vessel by slightly withdrawing the syringe plunger.

While the preferred embodiments have been shown and described, it will be understood that there is no intent to limit the invention by such disclosure, but rather, is intended to cover all modifications and alternate constructions falling within the spirit and scope of the invention as defined in the appended claims.

The invention claimed is:

1. A needle stick protection device, comprising:
a housing shaped and dimensioned for positioning about a syringe with an attached needle, the housing includes a first housing member telescopically coupled to a second housing member;
the first housing member including an open first end shaped and dimensioned for receiving the syringe and attached needle and an open second end, the first housing member including a first longitudinally extending slot;
the second housing member including an open first end and a substantially closed second end, the second end including an aperture shaped and dimensioned to permit the passage of a needle therethrough, the second housing member including a first detent extending through the first slot, wherein the second housing member further includes a slide actuating portion secured to the first detent of the second housing member facilitating controlled movement of the second housing member relative to the first housing member;
a locking member associated with the first slot of the first housing member for selectively engaging the first detent to control positioning of the second housing member relative to the first housing member; the locking member includes a first lateral recess formed within the first slot for seating of the first detent when the second housing member is in its forward most position, the first lateral recess being circumferentially located along a side of the first slot, and the locking member further includes a first spring biased lock arm composed of a cantileavered beam which circumferentially forces the first detent within the first lateral recess when the second housing member is in its forward most position fully extended relative to the first housing member so that the needle is fully covered by the second housing member; wherein the needle may be selectively covered and uncovered by selective alignment of the first detent with the slot in a manner permitting controlled motion of the first housing member relative to the second housing member; and
a spring positioned between the second end of the first housing member and the first end of the second housing member, the spring urging the first housing member and the second housing member to a fully telescoped position in which the needle is exposed.

2. The needle stick protection device according to claim 1, wherein the housing is transparent.

3. The needle stick protection device according to claim 1, wherein the first housing member further includes a second longitudinally extending slot and the second housing member further includes a second detent extending through the second slot.

4. The needle stick protection device according to claim 3, wherein the locking member further includes a second lateral recess formed within the second slot for seating of the second detent when the second housing member is in its forward most position and a second spring biased lock arm biasing the second detent within the second lateral recess when the second housing member is in its forward most position.

5. The needle stick protection device according to claim 4, wherein the first and second spring biased lock arms are respective cantileavered beams.

6. The needle stick protection device according to claim 1, wherein the first housing member includes means for selectively attaching to a syringe.

7. The needle stick protection device according to claim 6, wherein the means for selective attachment includes a pair of opposed slots at the first end of the first housing member, the opposed slots being shaped and dimensioned for receipt of the syringe.

8. The needle stick protection device according to claim 1, wherein the slide actuating portion is a thumb pad.

* * * * *